US009360563B2

(12) United States Patent
Perna (10) Patent No.: US 9,360,563 B2
(45) Date of Patent: Jun. 7, 2016

(54) SCINTILLATION DETECTOR ASSEMBLY (71) Applicant: Saint-Gobain Ceramics & Plastics, Inc., Worcester, MA (US)

(72) Inventor: Louis Perna, Elyria, OH (US)

(73) Assignee: SAINT-GOBAIN CERAMICS & PLASTICS, INC., Worcester, MA (US)

( * ) Notice: Subject to any disclaimer, the term of this patent is extended or adjusted under 35 U.S.C. 154(b) by 64 days.

(21) Appl. No.: 14/179,945

(22) Filed: Feb. 13, 2014

(65) Prior Publication Data

US 2014/0158891 A1 Jun. 12, 2014

Related U.S. Application Data (63) Continuation of application No. 12/861,221, filed on Aug. 23, 2010, now abandoned.

(60) Provisional application No. 61/236,294, filed on Aug. 24, 2009.

(51) Int. Cl.
*G01T 1/20* (2006.01)
*A61B 6/03* (2006.01)
*A61B 6/00* (2006.01)

(52) U.S. Cl.
CPC ............... *G01T 1/2006* (2013.01); *G01T 1/20* (2013.01); *G01T 1/2002* (2013.01); *A61B 6/037* (2013.01); *A61B 6/4258* (2013.01); *Y10T 156/10* (2015.01)

(58) Field of Classification Search
CPC ....... G01T 1/20; G01T 1/2002; G01T 1/2006; A61B 6/037; A61B 6/4258
See application file for complete search history.

(56) References Cited

U.S. PATENT DOCUMENTS

| | | | |
|---|---|---|---|
| 4,720,426 A | 1/1988 | Englert et al. | |
| 5,276,328 A | 1/1994 | Yoshida et al. | |
| 5,378,894 A | 1/1995 | Akai | |
| 6,298,113 B1 | 10/2001 | Duclos et al. | |
| 6,393,092 B1 | 5/2002 | Yoshida | |
| 7,019,297 B2 | 3/2006 | Aykac et al. | |
| 7,402,809 B2 | 7/2008 | Minagawa et al. | |
| 2004/0124362 A1 | 7/2004 | Hennessy et al. | |
| 2004/0140431 A1 | 7/2004 | Schmand et al. | |
| 2005/0016950 A1 | 1/2005 | Andreaco et al. | |

(Continued)

FOREIGN PATENT DOCUMENTS

| | | |
|---|---|---|
| CN | 1673773 A | 9/2005 |
| CN | 1804660 A | 7/2006 |
| JP | S6325579 A | 2/1988 |

(Continued)

OTHER PUBLICATIONS

Barton et al. "Scintillator Geometry and Surface Treatment for Readout by a Small Area Silicon Photomultiplier," 2007 IEEE Nuclear Science Symposium Conference Record, p. 1269-1274.

(Continued)

*Primary Examiner* — Casey Bryant
(74) *Attorney, Agent, or Firm* — Abel Law Group, LLP (57) ABSTRACT

The present disclosure relates to a scintillation assembly. The assembly may include a scintillator having a surface, a pressure sensitive adhesive layer contacting at least a portion of said surface, and a reflector proximal to the scintillator surface and adhered to the scintillator surface by the pressure sensitive adhesive layer, wherein the adhesive layer exhibits a TTV of 0.01 mm or less.

20 Claims, 5 Drawing Sheets

(56) References Cited

U.S. PATENT DOCUMENTS

2005/0211906 A1 9/2005 Tonami et al.
2005/0285045 A1 12/2005 Baumgartner et al.

FOREIGN PATENT DOCUMENTS

| JP | 2001349949 A | 12/2001 |
| JP | 2003191365 A | 7/2003 |

OTHER PUBLICATIONS

"Optically Clear Laminating Adhesive 8142: Product Data Sheet" 3M Tapes & Adhesives Group, 3M United Kingdom Plc, Jul. 2000, 2 pgs.

Epoxy Technology. "Epo-tek 301-2". accessed Aug. 28, 2012. <http://www.epotek.com>.

International Search Report dated Apr. 21, 2010, received in international patent application No. PCT/US2010/046279, 3 pages.

SCINTILLATION DETECTOR ASSEMBLY

RELATED APPLICATION

This application claims the benefit of U.S. patent application Ser. No. 12/861,221 filed on Aug. 23, 2010 and titled SCINTILLATION DETECTOR ASSEMBLY, which in turn claims the benefit of U.S. Provisional Patent Application Ser. No. 61/236,294 filed on Aug. 24, 2009 and titled SCINTILLATOR DETECTOR ASSEMBLY. Both of the applications are incorporated herein by reference in their entirety.

FIELD OF THE INVENTION

The present disclosure relates to a scintillator assembly for use in a scintillation detector, wherein the assembly includes a scintillator having a surface, a pressure sensitive adhesive layer contacting at least a portion of the surface, and a reflector proximal to the scintillator surface and adhered to the scintillator surface by the pressure sensitive adhesive layer. The adhesive layer may exhibit a TTV of 0.01 mm or less.

BACKGROUND

Scintillation detectors may generally be used to detect relatively high energy photons, electrons or alpha particles wherein high energy may be 1 KeV or higher, including $\alpha$-particles or $\beta$-particles. It may be appreciated that these photons, electrons or alpha particles may not be easily detected by conventional photodetectors, which may, for example, be sensitive to photons at wavelengths of 200 nm or greater, including 200 nm to 800 nm. A scintillator, or scintillation crystal, ceramic or plastic, may absorb ionizing waves or particles and convert the energy of the waves or particles to a light pulse. The light may be converted to electrons (i.e., an electron current) with a photodetector such as a photodiode, charge coupled detector (CCD) or photomultiplier tube. Scintillation detectors may be used in various industries and applications including medical (e.g., to produce images of internal organs), geophysical (e.g., to measure radioactivity of the earth), inspection (e.g., non-destructive, non-invasive testing), research (e.g., to measure the energy of photons and particles), and health physics (e.g., to monitor waves or particles in the environment as it affects humans).

Scintillation detectors may typically include either a single scintillator or a number of scintillators arranged in an array (also referred to herein as a scintillator). Many scanning instruments may include scintillation detectors that may be comprised of pixellated arrays of scintillators. Arrays may consist of a single row of adjoining scintillator pixels (linear array) or multiple rows and columns of adjoining scintillator pixels (2-D array). Linear and 2-D arrays may include thousands of scintillator pixels and the system may be constructed and arranged so that an emission from each pixel can be individually detected by a photodetector.

Individual scintillators within a scintillation detector may be covered on one or more sides by a reflector that may reflect light generated by a scintillator back into the scintillator, increasing the detectable signal. Reflectors may also be utilized to prevent cross-talk between scintillators in an array, i.e., prevent light generated by a scintillator from entering another scintillator in the array. A reflector may be positioned proximal to the scintillator by an adhesive. The adhesive may be applied as a polymer precursor that may be cured once applied to the scintallator. The scintillators including the reflectors may then be assembled into an array or provided as a single scintillator, which may then be positioned within the scintillation detector.

SUMMARY OF THE INVENTION

An aspect of the present disclosure relates to a scintillation assembly. The assembly may include a scintillator having a surface, a pressure sensitive adhesive layer contacting at least a portion of the surface, and a reflector proximal to the scintillator surface and adhered to the scintillator surface by the pressure sensitive adhesive layer. The adhesive layer may exhibit a TTV of 0.01 mm or less.

Another aspect of the present disclosure relates to a method of forming a scintillation device. The method may include adhering a reflector to at least a portion of a surface of a scintillator. The reflector may be adhered to the scintillator surface by an adhesive layer, wherein may exhibit a TTV of 0.01 mm or less.

A further aspect of the present disclosure relates to a scintillation detection system. The system may incorporate a scintillator assembly including a scintillator having a surface, a pressure sensitive adhesive layer contacting at least a portion of the surface, and a reflector proximal to the scintillator surface and adhered to the scintillator surface by the pressure sensitive adhesive layer, wherein the adhesive layer exhibits a TTV of 0.01 mm or less. The system may also incorporate a photodetector in optical communication with the scintillator and an analyzer in electrical communication with the photodetector.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein:

FIG. 4b illustrates adhesive positioned over the series of scintillators of FIG. 4a;

DETAILED DESCRIPTION

The present disclosure relates to an adhesive for positioning a reflector proximal to a surface of a scintillator in a scintillator assembly. The scintillator assembly may include one or more scintillators, which may be positioned in a scintillation detector. Furthermore, the scintillation detector may be positioned within a device or an apparatus such as a medical device, an inspection apparatus, a research device, etc.

The scintillator may be sensitive to relatively high energy photons, electrons, or alpha particles, wherein high energy may be understood as being 1 KeV or greater including, but not limited to γ-rays or x-rays, as well as β-particles or α-particles. Upon absorbing such radiant energy, a scintillator may, in response, emit a light pulse. The light pulse may exhibit a maximum wavelength of emission in the range of 200 nm to 600 nm, including all values and increments therein. In addition, the light pulse may have a decay time in the range of 0.1 ns to 20000 ns, including all values and increments therein. The light pulse may then pass through the scintillator, which may be relatively transparent to one or more wavelengths of the light emitted by the scintillator. When provided in, for example, a detector, the light pulses may be converted into electrical signals via a photodetector.

The scintillators may be formed from inorganic or organic materials. Examples of inorganic scintillators may include crystals such as thallium doped sodium iodide (NaI(Tl)) or thallium doped cesium iodide (CsI(Tl)). Additional examples of scintillation crystals may include barium fluoride, cerium-doped lanthanum chloride ($LaCl_3(Ce)$), bismuth germinate ($Bi_4Ge_3O_{12}$), cerium-doped yttrium aluminum garnet (Ce:YAG), cerium-doped lanthanum bromide ($LaBr_3(Ce)$), lutetium iodide ($LuI_3$), calcium tungstate ($CaWO_4$), cadmium tungstate ($CdWO_4$), lead tungstate ($PbWO_4$), zinc tungstate ($ZnWO_4$) or lutetium oxyorthosilicate ($Lu_2SiO_5$), as well as cerium doped-lutetium yttrium oxyorthosilicate ($Lu_{1.8}Y_{0.2}SiO_5(Ce)$). Scintillators may also include inorganic ceramics such as terbium-doped gadolinium oxysulfide (GOS(Tb)), or europium doped lutetium oxide ($Lu_2O_3(Eu)$). In addition, examples of organic scintillators may include polyvinyltoluene (PVT) with organic fluors present in the PVT as well as other polymer materials.

Figure 1:
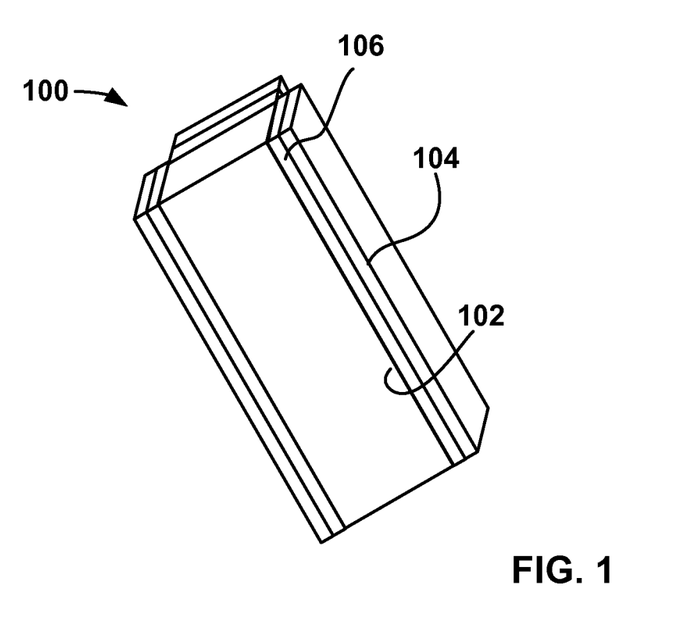
FIG. 1 illustrates an example of an arrangement of a scintillator in a scintillation assembly.

FIG. 1 illustrates an example of an arrangement of a scintillator in a scintillation assembly. The scintillator 100 may include one or more surfaces 102. Reflectors 104 may be provided proximal to at least a portion of one or more of the scintillator surfaces. As alluded to above, the reflectors may reflect light generated by a scintillator back into the scintillator and/or towards a photodiode, which may increase the detectable signal. Reflectors may also be utilized to prevent cross-talk between scintillators in an array, i.e., prevent light generated by a scintillator from entering another scintillator in the array.

The reflectors may be formed of materials exhibiting specular and/or diffuse reflection. Specular reflection may be understood as the reflection of light from a single incoming angle to a single outgoing angle. Diffuse reflection may be understood as the reflection of light from a single incoming angle to multiple outgoing angles. The reflector may be capable of exhibiting a total reflectance (reflectance of both diffuse and specular origins) of at least 80% or more of incident light, including all values and increments in the range of 80% to 99% at a wavelength of 340 nm to 800 nm. Examples of reflective materials may include aluminum, aluminum oxide, or fluoropolymers, such as polytetrafluoroethylene, which may be available under the tradename TEFLON from DUPONT.

The reflector may be positioned proximal to the scintillator by an adhesive 106. In some examples, the adhesive may be coated onto or applied to the reflector, forming a single or double sided tape that may be applied to a scintillator. In other examples, the adhesive may be coated onto or applied to the scintillator and the reflector may be applied to the coated scintillator surface. The coatings may be applied by a process such as spray coating, dip coating, roll coating, gravure coating, etc. In addition, one or more sides of a reflector or scintillator may be coated. In coating scintillators, it may be necessary to mask some surfaces of the scintillators, such as the ends of the scintillator or one or more sides of the scintillator. In other examples, the adhesive may include a film or sheet, wherein the sheet may be adhered to one or more sides of a reflector.

In some examples, the adhesive may be a pressure sensitive adhesive. Pressure sensitive may be understood as an adhesive that adheres when contacted with a substrate (i.e., a scintillator or reflector) with a degree of pressure. It may be appreciated that the amount of pressure may vary widely depending on the adhesive and may be, for example, 0.0001 $kgf/mm^2$ or greater. In some examples, adhesion may be facilitated by mechanical or chemical forces. For example, where adhesion is facilitated by mechanical forces, it may be due to interlocking of the adhesive material to pores or other features in the substrate. Chemical adhesion may be due to ionic bonding, covalent bonding, hydrogen bonding or van der Waals forces.

The adhesive may be formed from thermoplastic polymers or copolymers, monomers or oligomers. In some examples, the adhesive may be formed from natural or synthetic rubber based materials. In other examples, the adhesive may be formed of one or more acrylic type monomers, oligomers or polymers, such as acrylate and/or (meth)acrylate type monomers, oligomers, or polymers. The adhesive may also be formed of copolymer or terpolymer systems such as acrylic type or synthetic rubber type systems. In further examples, the adhesive may be cross-linked and may include cross-linking agents, initiators and/or chain transfer agents. The adhesive may also optionally include tackifiers, plasticizers, fillers, anti-oxidants, foaming agents, solvents, stabilizers, fire retardants, viscosity enhancing agents, fibrous reinforcing agents and other additives.

Figure 2:
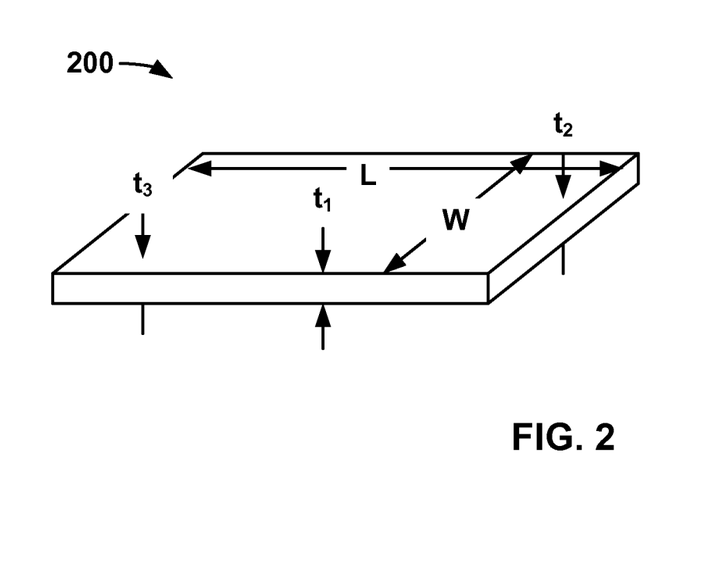
FIG. 2 illustrates an example of a sheet of adhesive contemplated herein.

The adhesive may have a thickness of 0.1 mm or less, including all values and increments in the range of 0.001 mm to 0.1 mm. In some examples, the adhesive thickness may be 0.075 mm or less, such as in the range of 0.025 mm to 0.075 mm, including all values and increments therein. The thickness of the adhesive may vary +/−5% or less, including all values and increments therein. Stated another way, the total thickness variation (TTV) of the adhesive may be 0.01 mm or less, including all values and increments in the range of 0.001 mm to 0.01 mm. Total thickness variation may be understood as the difference between maximum and minimum thickness values of an adhesive layer determined from the measurement of a number of points, which may be chosen in a random or preselected pattern. The total thickness variation may be expressed as the difference between the maximum thickness ($T_{max}$) and the minimum thickness ($T_{min}$), wherein $TTV=T_{max}-T_{min}$. For example, as illustrated in FIG. 2, the adhesive 200 may exhibit a first thickness at a given point $t_1$, a second thickness at a second given point $t_2$, and a third thickness at a third given point $t_3$, and so on, up to $t_n$. The TTV may be understood as the difference of the maximum thickness of points $t_1$-$t_n$ and the minimum thickness of points $t_1$-$t_n$. In addition, it may be appreciated that for any given area, the adhesive may be present at a relatively consistent volume, wherein the volume of adhesive may vary +/−5% or less for such given areas. An example of an adhesive may be available from Hillas Packaging of Fort Worth Tex. under the Product Description of 3M 8142 Optically Clear Adhesive.

In addition, in some examples, the adhesive may transmit 90% or more of incident light, including all values and increments in the range of 90% to 99.9%, wherein the light exhibits a wavelength in the range of 340 nm to 800 nm. Incident light may be understood as light that falls on a surface. The adhesive may also exhibit a refractive index of 1.00 to 1.60, including all values and increments therein, such in the range of 1.40 to 1.50, 1.47, 1.49, etc., when measured at a wavelength of 633 nm. In some examples, the refractive index may be in the range of 1.4740 to 1.4750, measured at a wavelength of 633 nm. Refractive index may be understood as the ratio of the velocity of light in a vacuum to light in a given material. Furthermore, the adhesive may exhibit a haze of 10% or less, including all values and increments in the range of 0.01% to 10%, at a wavelength in the range of 340 nm to 800 nm. In some examples, haze may be in the range of 0.1 to 0.8%. Haze may be generally understood as the degree of cloudiness of a given material and, more specifically, may be understood as the reciprocal of light transmission or the percentage of transmitted light that, in passing through a given material, deviates from the incident beam. It may be appreciated that the thickness of the adhesive may affect properties such as optical transmission, haze or refractive index. For example, at thicknesses in the range of 0.01 mm to 0.75 mm, the refractive index may be in the range of 1.4740 to 1.4750 at 633 nm, the haze may be in the range of 0.1% to 0.8% and the total luminous transmission may be greater than 90% as measured by ASTM E903, D1003 and E284.

The adhesive may contact at least 20% or more of a given scintillator surface, including all values and increments therein, such as in the range of 20% to 100%, 25% to 85%, 95% to 99%, etc. It may be appreciated that in a given scintillator assembly, the adhesive may contact different amounts of the various surfaces or may contact the same amounts of the various surfaces. It may also be appreciated that when a portion (i.e., 20% or more) of the surface is contacted by the adhesive, gapping or bubbling between the adhesive and the surface may be minimal and may prevent or minimize the escape of air during downstream processes in forming the scintillation detector as further discussed below.

Figure 3A:
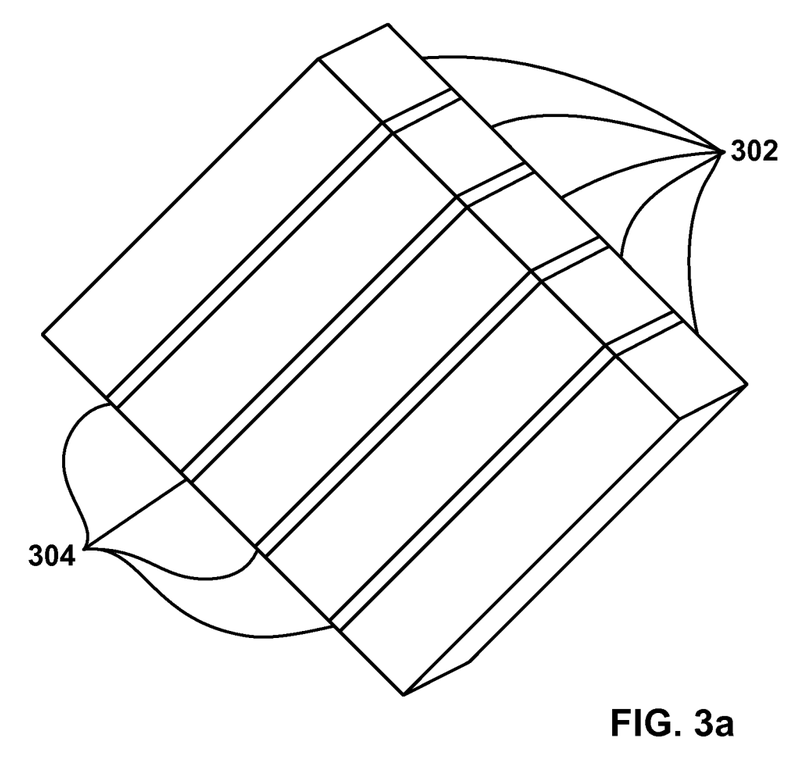
FIG. 3a illustrates an example of a one dimensional array.
Figure 3B:
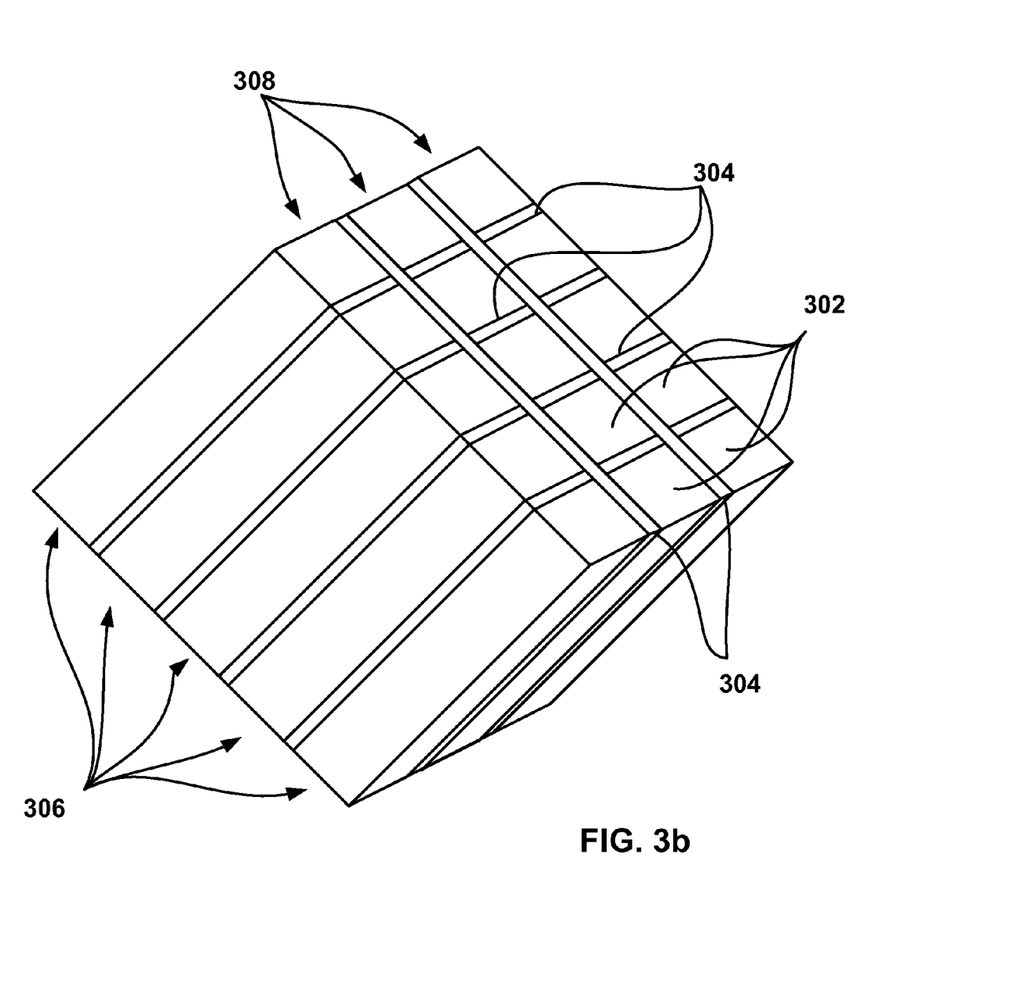
FIG. 3b illustrates an example of a two dimensional array.

It may also be appreciated that the scintillator assemblies may be provided in an array, such as one dimensional or two dimensional arrays. For example, as illustrated in FIG. 3a, a series of scintillators 302 may be provided in a one dimensional array including reflectors 304 positioned around a number of surfaces of the scintillators 302. FIG. 3b illustrates a two dimensional array, wherein the scintillators 302 may be arranged in a number of columns 306 and rows 308.

In some examples, the scintillator assemblies may be formed by positioning a first side of an adhesive layer over a portion of a scintillator surface and positioning a reflector proximal to the scintillator surface by contacting the reflector with the second side of the adhesive. The adhesive layer may be formed by coating an adhesive onto the scintillator or reflector surface or by positioning an adhesive sheet over the scintillator or reflector surface. In other examples, the scintillator assemblies may be formed by forming rows of scintillators, positioning an adhesive and/or a reflector onto the scintillators, wherein the scintillator, adhesive and reflector may be cut into individual scintillator assemblies and, in some cases, stacked into an array. Once again, the adhesive may be positioned by coating the scintillator surface or reflector surface with the adhesive.

Figure 4A:
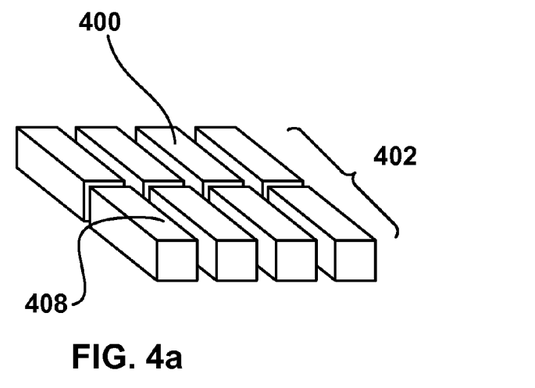
FIG. 4a illustrates an example of a series of scintillators positioned together.
Figure 4B:
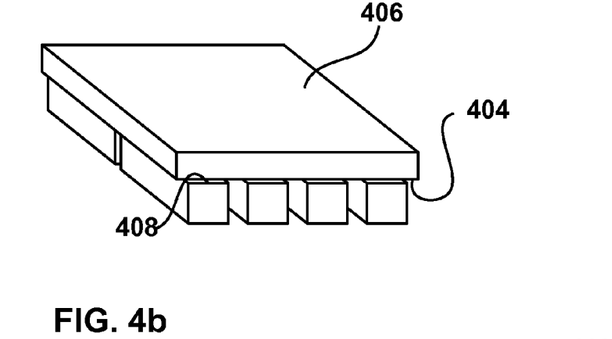
Figure 4C:
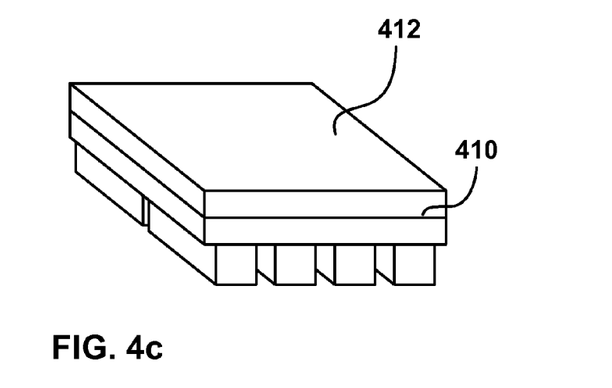
FIG. 4c illustrates a reflector material positioned over the series of scintillators of FIG. 4b.

For example, the scintillators 400 may be arranged in a series, such as by positioning the scintillators relatively closely together in one or more rows 402, as illustrated in FIG. 4a. A first side 404 of the adhesive 406 may then be applied to a surface 408 of each scintillator in the row or rows of scintillators FIG. 4b. The adhesive may be provided by coating an adhesive layer onto the surface 408 or the adhesive may be provided as a sheet on at least one backing or liner and in some cases, a second backing may be provided on the other side of the adhesive sheet as well. When applying the adhesive as a sheet, one surface of the adhesive sheet may be exposed and contacted with the scintillator surfaces. Pressure may be applied to the adhesive sheet, such as with a roller, knife or a press. The second surface of the adhesive 410 may then be exposed and the reflector material 412 may be positioned over and contacted with the adhesive sheet as illustrated in FIG. 4c. Pressure may again be applied. The scintillators, including the reflective layer may be cut apart and excess adhesive and/or reflector material may then be trimmed. Additional rows of scintillators may be formed, wherein adhesive may be applied and the scintillators may again be separated. These scintillators may be adhered to the scintillators including the reflective layers, also forming a number of rows. The process may be repeated until a desired array may be formed. It should be appreciated that reference herein to scintillator implies both a single scintillator and scintillator assemblies (scintillator arrays) including one or more scintillators.

The assembled scintillator may then be affixed to a light guide, which may then be affixed to a photomultiplier. In some examples, the light guide may be formed of or adhered by a curable polymeric material, such as a silicone polymer, wherein curing may occur upon the application of heat and/or vacuum. As may be appreciated, the reduction of gapping or bubbling between the adhesive and scintillators or reflectors may prevent the escape of air into the polymeric material during the curing process, which escaped air may form air bubbles. Exemplary cure temperatures may be in the range of 50° C. to 200° C., including all values and increments therein, and exemplary cure times may be in the range of 10 minutes to 24 hours, including all values and increments therein.

In other examples, the scintillator may be affixed to the light guide using the pressure sensitive adhesive, which may act to affix the light guide to the photomultiplier. It may therefore be appreciated that the ability to separately form the light guide in a vacuum and adhere the light guide to the scintillator may prevent the formation of air bubbles between the light guide and scintillator. Similarly, where an adhesive may be used as a light guide, the formation of air bubbles between the photomultiplier and scintillator may be reduced.

Figure 5:
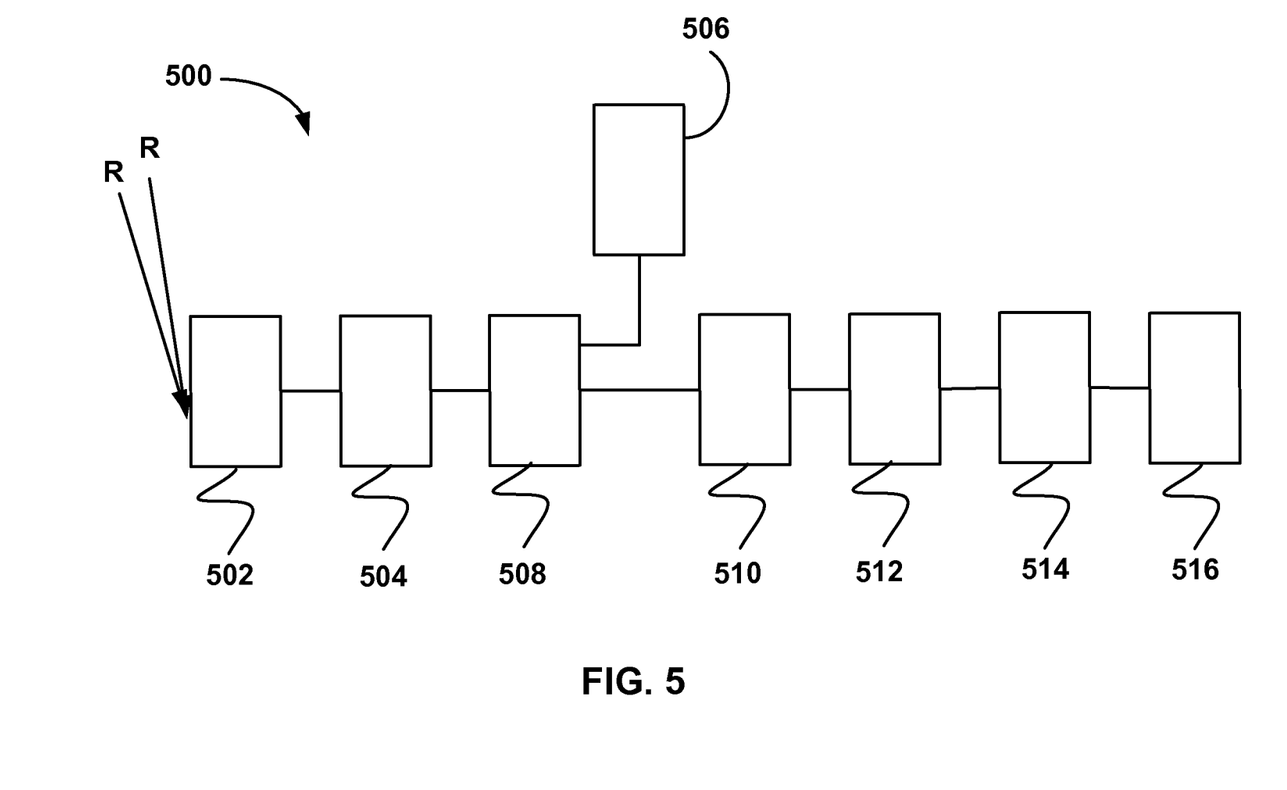
FIG. 5 illustrates an example of a scintillation detector.

The assembled scintillator may then be positioned in a scintillator detector, an example of which is illustrated in FIG. 5. The scintillation detector 500 may include one or more scintillation arrays 502 and may generally be used to detect various waves or particles R that may not be easily detected by conventional photodetectors. The scintillator 502, or scintillation crystal, ceramic or polymer, may absorb ionizing waves or particles and convert the energy of the waves or particles to a light pulse. The light may be converted to electrons (i.e., an electron current) with a photodetector 504 such as a photodiode, charge coupled detector (CCD) or photomultiplier tube.

In one example, the photodetector 504 may be a photomultiplier tube (PMT). As photons emitted from the scintillator strike a photocathode within the photomultiplier tube, electrons may be generated producing a signal representative of the incident waves or particles absorbed by the scintillator. The photomultiplier 504 may be biased by a high voltage power supply 506, which connects to a voltage divider 508. The voltage divider 508 may divide the high voltage into a series of steps to accelerate the electrons from one photomultiplier stage to the next. The photomultiplier may multiply or amplify the signal produced by at least a few orders of magnitude, such as in the range of $10^2$ to $10^8$.

The signal provided by the photodetector 504 may then be processed by a pre-amplifier 510 and an amplifier 512, an analog to digital converter 512 and then by a multi-channel analyzer 516 to which the photodetector 504 may be in electrical communication. In one example, the pre-amplifier may amplify or increase the signal received from the photodetector and the amplifier may shape or filter the signal received from the pre-amplifier. However, it may be appreciated that other arrangements may be utilized herein as well.

It may be appreciated that scintillators and/or scintillator arrays have been assembled using two component adhesive systems and/or curable adhesive systems, such as epoxy or acrylic systems. Such systems may, and have been found, to exhibit a number of drawbacks in the formed array, including dimensional instability and/or inconsistency between the scintillator/adhesive/reflector layers, which may reduce the accuracy or precision of the measurements made by the scintillator or scintillator array. For example, excess adhesive may be provided, which may accumulate on the scintallator or between the scintillator and reflector creating thickness variations in the overall scintillator or array. In some cases, the scintillator may be too small or too thick for its intended use or the pixels created by the individual scintillators in an array may not be properly or evenly spaced. In other examples, too little adhesive may be applied, forming gaps or air bubbles, which may affect the optical characteristics of the scintillator. Furthermore, where application of the adhesive may be uneven, exhibiting relatively high points and relatively low points, the adhesive may pull away from either the scintillator itself or the reflector, which may be damaging to either component, also potentially creating issues with the size of the assembled scintillator or array as well as the optical characteristics of the array.

The use of such systems may also complicate the manufacturing process. For example, adhesive viscosity may vary during start ups or shut downs or upon environmental changes, including changes in temperature or humidity. In addition, errors in application of the adhesive may occur, again reducing the consistency of the adhesive layer thickness. Furthermore, the adhesive may expand and/or contract during or after cure or solidification causing dimensional changes in the array. In other examples, where excess adhesive may be applied, removal may require an excess amount of force or the use of relatively harsh solvents, potentially detrimentally damaging the scintillator and or reflector.

It may also be appreciated, that as the number of layers of adhesive increases, the variations in the adhesive layer thickness may accumulate causing even broader variations in the final scintillator assembly, including as described above, the product being too thick or too thin or exhibiting uneven pixel spacing within an array. In addition, as the number of layers in an array increase, the amount of time necessary to construct an array may increase. It may be appreciated that in assembly with an adhesive system requiring cure or solidification, one may need to wait until the adhesive has minimally reached its solidification point or gel point prior to proceeding with a subsequent layer. Once again, the above problems may cause issues with respect to the size of the scintillator assembly as well as the optical characteristics of the assembly.

In utilizing a pressure sensitive adhesive system exhibiting a controlled thickness as described above, adhesive uniformity and total thickness variation may be improved, wherein problems associated with variations in adhesive thickness, described above, and/or gaps may be reduced. In addition, pressure sensitive systems may allow for relatively easy removal of excess adhesive that may be provided on a surface. That is, less pressure may be necessary to remove excess adhesive, without the use of cutting devices. Whereas, in removing cured or solidified polymer, sharp devices may be necessary that may cause nicks in the scintillator. Furthermore, manufacturing may be improved. For example, it may not be necessary to wait for the adhesive to cure or solidify to a given point before moving to the next manufacturing step, such as adding a scintallator, adhesive or reflector layer. In addition, reduction of gaps between the adhesive and the scintillator and/or reflector may reduce air bubbles in the scintillator assembly and resulting detector. Increasing thickness uniformity and reducing gaps may therefore increase the uniformity of scintillator spacing in an array and/or optical characteristics. Accordingly, the use of a pressure sensitive adhesive system may provide improvements in the manufacturing process as well in the resulting assembly.

Scintillation detectors may be used in various industries and applications including medical (e.g., to produce images of internal organs), geophysical (e.g., to measure radioactivity of the earth), inspection (e.g., non-destructive, non-invasive testing), research (e.g., to measure the energy of photons and particles), and health physics (e.g., to monitor waves or particles in the environment as it affects humans). Medical devices may include positron emission tomography scanners, gamma cameras, computed tomography scanners and/or radioimmunoassay applications. Geophysical devices may include well logging detectors. Inspection devices may include radiance detectors, such as thermal neutron activation analysis detectors, luggage scanners, thickness gauges, liquid level gauges, security and manifest verification devices both active and passive, spectroscopy devices (radioisotope identification devices) both active and passive devices, and/or gross counters both active and passive. Research devices may include spectrometers and calorimeters. Health physics applications may include laundry monitoring and area monitoring.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A scintillation assembly, comprising:
   a first scintillator having a first photodetector surface and a first side surface adjacent to said first photodetector surface;
   a second scintillator having a second photodetector surface and a second side surface adjacent to said second photodetector surface;
   a first pressure sensitive adhesive layer directly contacting at least a portion of said first and second side surfaces, wherein the first pressure sensitive adhesive includes an optically clear pressure sensitive adhesive comprising acrylic;
   a diffuse reflector including a fluoropolymer proximal to said first and second side surfaces and adhered to said first and second side surfaces by said first pressure sensitive adhesive layer, wherein:
   said first and second scintillators are disposed along a same side of said reflector;
   said first pressure sensitive adhesive layer is disposed between said reflector and said first side surface;
   said first pressure sensitive adhesive layer is disposed between said reflector and said second side surface; and
   said first pressure sensitive adhesive layer has a thickness in a range of 0.02 mm to 0.1 mm, exhibits a TTV of 0.01 mm or less and transmits 90% or more of incident light having a wavelength in a range of 340 nm to 800 nm.

2. The scintillation assembly of claim 1, wherein said first pressure sensitive adhesive layer comprises a sheet of adhesive including a first side and a second side, wherein said first side is adhered on at least a portion of said first and second side surfaces and said second side is adhered to said reflector.

3. The scintillation assembly of claim 1, further comprising:
a third scintillator having a third photodetector surface and a third side surface adjacent to said third photodetector surface;
a fourth scintillator having a fourth photodetector surface and a fourth side surface adjacent to said fourth photodetector surface; and
a second pressure sensitive adhesive layer directly contacting at least a portion of said third and fourth side surfaces, wherein said second pressure sensitive adhesive includes an optically clear pressure sensitive adhesive and said reflector is adhered to said third and fourth side surfaces by said second pressure sensitive adhesive layer.

4. The scintillation assembly of claim 1, wherein said first pressure sensitive adhesive layer exhibits a refractive index of 1.00 to 1.60 at a wavelength of 630 nm.

5. The scintillation assembly of claim 1, wherein said first pressure sensitive adhesive layer exhibits a haze of 10% or less at a wavelength in the range of 340 nm to 800 nm.

6. The scintillation assembly of claim 1, wherein said first pressure sensitive adhesive layer has a thickness of 0.025 mm to 0.075 mm.

7. The scintillation assembly of claim 1, wherein said diffuse reflector comprises polytetrafluoroethylene.

8. The scintillation assembly of claim 1, wherein said scintillator assembly is present in a medical device.

9. The scintillation assembly of claim 1, wherein said scintillator assembly is present in a well logging detector.

10. The scintillation assembly of claim 1, wherein said scintillator assembly is present in an inspection apparatus.

11. The scintillation assembly of claim 10, wherein said inspection apparatus is selected from the group consisting of a thermal neutron activation analysis detector, luggage scanner, thickness gauge, liquid level gauge, active security device, active manifest verification device, passive security device, passive manifest verification device, active spectrometer, passive spectrometer, active gross counter and passive gross counter.

12. The scintillation assembly of claim 1, wherein said scintillator assembly is present in a research device.

13. A method of forming a scintillation device, the method comprising:
providing a first scintillator and a second scintillator, wherein:
said first scintillator having a first photodetector surface and a first side surface adjacent to said first photodetector surface;
said second scintillator having a second photodetector surface and a second side surface adjacent to said second photodetector surface; and
adhering a diffuse reflector including a fluoropolymer to at least a portion of said first side surface of said first scintillator and said second side surface of said second scintillator, wherein
said diffuse reflector is adhered to said first and second side surfaces by a pressure sensitive adhesive layer that directly contacts said first and second side surfaces, wherein:
said first and second scintillators are disposed along a same side of said reflector; and
said pressure sensitive adhesive layer includes an optically clear pressure sensitive adhesive comprising acrylic and has a thickness in a range of 0.02 mm to 0.1 mm, exhibits a TTV of 0.01 mm or less, transmits 90% or more of incident light having a wavelength in a range of 340 nm to 800 nm, and is disposed between said reflector and said first and second side surfaces.

14. The method of claim 13, wherein said pressure sensitive adhesive layer is an adhesive sheet.

15. The method of claim 13, wherein said pressure sensitive adhesive layer exhibits a refractive index of 1.47 at a wavelength of 630 nm.

16. The method of claim 13, wherein said pressure sensitive adhesive layer exhibits a haze of 10% or less at a wavelength in the range of 340 nm to 800 nm.

17. The method of claim 13, wherein said diffuse reflector comprises polytetrafluoroethylene.

18. A scintillation detection system, comprising:
a scintillator assembly including:
a first scintillator having a first photodetector surface and a first side surface adjacent to said first photodetector surface;
a second scintillator having a second photodetector surface and a second side surface adjacent to said second photodetector surface;
a first pressure sensitive adhesive layer directly contacting at least a portion of said first and second side surfaces, wherein the first pressure sensitive adhesive includes an optically clear pressure sensitive adhesive; and
a diffuse reflector comprising a fluoropolymer proximal to said first and second side surfaces and adhered to said first and second side surfaces by said first pressure sensitive adhesive layer, wherein:
said first and second scintillators are disposed along a same side of said reflector;
said first pressure sensitive adhesive layer is disposed between said reflector and said first side surface;
said first pressure sensitive adhesive layer is disposed between said reflector and said second side surface;
a third scintillator having a third photodetector surface and a third side surface adjacent to said third photodetector surface;
a fourth scintillator having a fourth photodetector surface and a fourth side surface adjacent to said fourth photodetector surface; and
a second pressure sensitive adhesive layer directly contacting at least a portion of said third and fourth side surfaces, wherein said second pressure sensitive adhesive includes an optically clear pressure sensitive adhesive and said reflector is adhered to said third and fourth side surfaces by said second pressure sensitive adhesive layer;
a photodetector in optical communication with said first, second, third, and fourth scintillators and adjacent to said first, second, third, and fourth photodetector surfaces; and
an analyzer in electrical communication with said photodetector,
wherein each of said first and second adhesive layers has a thickness in a range of 0.02 mm to 0.1 mm, exhibits a TTV of 0.01 mm or less and transmits 90% or more of incident light having a wavelength in a range of 340 nm to 800 nm.

19. The scintillation assembly of claim 18, wherein each of said first and second pressure sensitive adhesive layers has a thickness of 0.025 mm to 0.075 mm.

20. The scintillation assembly of claim 18, wherein said diffuse reflector comprises polytetrafluoroethylene.

* * * * *